US009138408B2

(12) United States Patent
Duranton et al.

(10) Patent No.: US 9,138,408 B2
(45) Date of Patent: Sep. 22, 2015

(54) USE OF TAURINE FOR TREATING ALOPECIA

(75) Inventors: Albert Duranton, Maisons-Laffitte (FR); Lionel Breton, Versailles (FR)

(73) Assignees: L'OREAL, Paris (FR); NESTEC S.A., Vevey (CH)

( * ) Notice: Subject to any disclaimer, the term of this patent is extended or adjusted under 35 U.S.C. 154(b) by 866 days.

(21) Appl. No.: 10/517,423

(22) PCT Filed: Jun. 23, 2003

(86) PCT No.: PCT/FR03/01919
§ 371 (c)(1),
(2), (4) Date: Mar. 10, 2005

(87) PCT Pub. No.: WO04/000293
PCT Pub. Date: Dec. 31, 2003

(65) Prior Publication Data
US 2005/0175565 A1 Aug. 11, 2005

(30) Foreign Application Priority Data

Jun. 21, 2002 (FR) ..................................... 02 07763
Jun. 21, 2002 (FR) ..................................... 02 07764
Jun. 21, 2002 (FR) ..................................... 02 07765

(51) Int. Cl.
*A61K 31/195* (2006.01)
*A61K 45/06* (2006.01)
*A61Q 7/00* (2006.01)
*A61K 9/00* (2006.01)
*A23L 1/30* (2006.01)
*A23L 1/305* (2006.01)
*A61K 8/46* (2006.01)
*A61K 8/63* (2006.01)
*A61K 8/86* (2006.01)
*A61K 9/20* (2006.01)
*A61K 9/48* (2006.01)
*A61K 31/185* (2006.01)

(52) U.S. Cl.
CPC ............ *A61K 9/0095* (2013.01); *A23L 1/3002* (2013.01); *A23L 1/3006* (2013.01); *A23L 1/3051* (2013.01); *A61K 8/466* (2013.01); *A61K 8/63* (2013.01); *A61K 8/86* (2013.01); *A61K 9/2054* (2013.01); *A61K 9/4858* (2013.01); *A61K 9/4866* (2013.01); *A61K 31/185* (2013.01); *A61K 31/195* (2013.01); *A61K 45/06* (2013.01); *A61Q 7/00* (2013.01); *A23V 2002/00* (2013.01); *A61K 2800/92* (2013.01)

(58) Field of Classification Search
CPC ............................... A61K 9/0095; A61Q 7/00
USPC ........................................................ 514/601
See application file for complete search history.

(56) References Cited

U.S. PATENT DOCUMENTS

| 459,812 | A | | 9/1891 | Considine |
|---|---|---|---|---|
| 4,139,619 | A | | 2/1979 | Chidsey, III |
| 5,223,285 | A | | 6/1993 | DeMichele et al. |
| 5,571,783 | A | | 11/1996 | Montagne et al. |
| 5,582,817 | A | * | 12/1996 | Otsu et al. ............... 424/59 |
| 5,582,839 | A | * | 12/1996 | McCarty ................ 424/489 |
| 5,601,806 | A | * | 2/1997 | Katsumata et al. ......... 424/59 |
| 5,605,929 | A | * | 2/1997 | Liao et al. ................ 514/456 |
| 5,639,785 | A | * | 6/1997 | Kung ...................... 514/456 |
| 5,648,377 | A | * | 7/1997 | Bombardelli et al. ..... 514/456 |
| 5,700,782 | A | | 12/1997 | Cope et al. |
| 5,895,652 | A | | 4/1999 | Giampapa |
| 5,976,568 | A | | 11/1999 | Riley |
| 6,103,272 | A | | 8/2000 | Keeney |
| 6,103,756 | A | | 8/2000 | Gorsek |
| 6,126,940 | A | * | 10/2000 | Takahashi et al. .......... 424/750 |
| 6,261,589 | B1 | | 7/2001 | Pearson et al. |
| 6,331,569 | B1 | | 12/2001 | Kisters et al. |
| 6,344,448 | B1 | * | 2/2002 | Brown ..................... 514/179 |
| 6,428,818 | B1 | * | 8/2002 | Morre et al. ............. 424/729 |
| 6,506,419 | B2 | | 1/2003 | Takahashi et al. |
| 6,514,544 | B2 | | 2/2003 | Fuchs et al. |
| 6,576,660 | B1 | | 6/2003 | Liao et al. |
| 6,685,970 | B1 | * | 2/2004 | Takahashi et al. .......... 424/725 |
| 6,696,484 | B2 | | 2/2004 | Liao et al. |
| 6,926,914 | B2 | | 8/2005 | Takahashi et al. |
| 2001/0033881 | A1 | | 10/2001 | Fuchs et al. |
| 2001/0036487 | A1 | | 11/2001 | Takahashi et al. |

(Continued)

FOREIGN PATENT DOCUMENTS

CN     1 322 552 A     11/2001
DE  202 04 844 U1      8/2002

(Continued)

OTHER PUBLICATIONS

Webster's Third Edition, 1963, G. and C. Merriam Company, p. 1798.*
Hamada, C. et al., "Cell Activator", JP 2002-097116, (Feb. 4, 2002), Machine Translation.*
Ruan, S., "Preparatio nof additive for food, medicine and cosmetics and replenishing linolic acid and gamma-linolenic acid", CN 1309926 A, Aug. 21, 2001, abstract.*
Takahashi, T., "Toxicological studies on procyanidin B-2 for external application as a hair growing agent", Food and Chemical Toxicology 37 (1999) 545-552.*

(Continued)

*Primary Examiner* — Gina Justice
(74) *Attorney, Agent, or Firm* — Oliff PLC

(57) ABSTRACT

The invention relates to a method of treating and preventing ageing of the pilosebaceous unit and/or alopecia in human through the administration of taurine and/or hypotaurine and/or the acceptable salts thereof in an oral composition. Specifically, the invention relates to a method of treating and preventing miniaturization of the hair follicle. The invention also relates to the use of polyphenols to achieve these same ends. Finally, the invention relates to oral compositions that include polyphenols or taurine and/or hypotaurine and/or the acceptable salts thereof as active ingredients.

44 Claims, 3 Drawing Sheets

(56) References Cited

U.S. PATENT DOCUMENTS

| | | |
|---|---|---|
| 2003/0105030 A1 | 6/2003 | Liao et al. |
| 2003/0138476 A1 | 7/2003 | Van Leeuwen et al. |
| 2003/0138510 A1 | 7/2003 | Takahashi et al. |
| 2003/0139385 A1 | 7/2003 | Song et al. |
| 2003/0144346 A1 | 7/2003 | Liao et al. |
| 2003/0153541 A1 | 8/2003 | Dudley et al. |
| 2006/0078595 A1 | 4/2006 | Van Leeuwen et al. |

FOREIGN PATENT DOCUMENTS

| | | | |
|---|---|---|---|
| EP | 0 064 012 A1 | 11/1982 | |
| EP | 0 211 610 A2 | 2/1987 | |
| EP | 0 277 428 A2 | 8/1988 | |
| EP | 0 334 586 A1 | 9/1989 | |
| EP | 0 353 123 A1 | 1/1990 | |
| EP | 0 356 271 A1 | 2/1990 | |
| EP | 0 375 388 A2 | 6/1990 | |
| EP | 0 403 238 A2 | 12/1990 | |
| EP | 0 408 442 A1 | 1/1991 | |
| EP | 0 420 707 A1 | 4/1991 | |
| EP | 0 459 890 A1 | 12/1991 | |
| EP | 0 519 819 A1 | 12/1992 | |
| EP | 0 522 964 A1 | 1/1993 | |
| EP | 0 614 616 A2 | 9/1994 | |
| EP | 0 652 012 A1 | 5/1995 | |
| EP | 1 116 489 A1 | 7/2001 | |
| EP | WO 2004/034820 * | 4/2004 | ............... A23L 1/30 |
| FR | 2 581 542 | 11/1986 | |
| FR | 2 734 477 A1 | 11/1996 | |
| IT | 1 218 115 | 4/1990 | |
| JP | A-62-084021 | 4/1987 | |
| JP | A-7-48270 | 2/1995 | |
| JP | A 7-233046 | 9/1995 | |
| JP | A-8-73350 | 3/1996 | |
| JP | A 9-59154 | 3/1997 | |
| JP | A 9-107917 | 4/1997 | |
| JP | A-10-7553 | 1/1998 | |
| JP | A-10-28553 | 2/1998 | |
| JP | A 10-99048 | 4/1998 | |
| JP | A 10-99048 | 4/1998 | |
| JP | A 11-292753 | 10/1999 | |
| JP | A-11-332514 | 12/1999 | |
| JP | A-2001-269148 | 10/2001 | |
| JP | A-2001-270881 | 10/2001 | |
| JP | A-2002-3371 | 1/2002 | |
| JP | 2002-97116 * | 2/2002 | |
| JP | A-2002-97116 | 4/2002 | |
| JP | A 2002-128651 | 5/2002 | |
| JP | A 2002-330748 | 11/2002 | |
| KR | 2001 000 741 A | 1/2001 | |
| KR | 2002 041 348 A | 6/2002 | |
| RU | 2 165 719 C1 | 4/2001 | |
| WO | WO 98/33472 | 8/1989 | |
| WO | WO 91/11117 A2 | 8/1991 | |
| WO | WO 94/02166 A1 | 2/1994 | |
| WO | WO 95/26646 A1 | 10/1995 | |
| WO | WO 99/22728 A1 | 5/1999 | |
| WO | WO 00/07607 A1 | 2/2000 | |
| WO | WO 00/18736 | 4/2000 | |
| WO | WO 00/30477 A1 | 6/2000 | |
| WO | WO 01/58283 A1 | 8/2001 | |
| WO | WO 02/24189 A1 | 3/2002 | |
| WO | WO 02/34262 A1 | 5/2002 | |
| WO | WO 02/096221 A2 | 12/2002 | |
| WO | WO 03/037320 A1 | 5/2003 | |

OTHER PUBLICATIONS

Takahashi, T. et al. "Procyanidin oligomers selectively and intensively promote proliferation of mouse hair epithelial cells In Vitro and active hair follicle growth in vivo", J. Invest. Dermatol. (1999) 112:310-316.*

Liao et al., "Growth Suppression of Hamster Flank Organs by Topical Application of Catechins, Alizarin, Curcumin, and Myristoleic Acid," Arch Dermatol.Res, vol. 293, pp. 200-205, 2001.

Shigematsu et al., "Inhibition of Collagen Hydroxylation by Lithospermic Acid Magnesium Salt, a Novel Compound Isolated from *Salviae Miltiorrhizae* Radix," Biochimica et Biophysica Acta, vol. 1200, pp. 79-83, 1994.

Bravo, "Polyphenols: Chemistry, Dietary Sources, Metabolism, and Nutritional Significance," Nutrition Reviews, vol. 56, No. 11, pp. 317-333, Nov. 1998.

Scalbert et al., "Dietary Intake and Bioavailibility of Polyphenols," American Society for Nutritional Sciences, pp. 2073S-2085S, 2000.

Kamimura, A., et al., "Investigation of Topical Application of Procyanidin B-2 from Apple to Identify its Potential Use as a Hair Growing Agent," Phytomedicine, 2000, vol. 7 (6), pp. 529-36. (Abstract).

Takahashi, T., et al., "The First Clinical Trial of Topical Application of Procyanidin B-2 to Investigate its Potential as a Hair Growing Agent," Phytother Res., 2001, vol. 15 (4), pp. 331-336. (Abstract).

Australian Office Action for corresponding Application No. 2007229399 issued Aug. 7, 2009.

Oct. 17, 2011 Third Party Observations in European Patent Application No. 10184434.8.

Sodhala; Gadanigrahah ed, Ganga Sahaya Pandeya & Com.—Indradeva Tripathi, Part-1 (Prayoga Khanda) Chaukhamba Sanskrit Sansthan, Varanasi, Ed. 3rd 1999, p. 183-184 (Formulation ID: AK2/287, Formulation Name: Brhat Pancanimbakam Curnam) (with translation).

Summary of Aug. 10, 2009 Japanese Office Action and Explanation of Cited References.

* cited by examiner

USE OF TAURINE FOR TREATING ALOPECIA

This application is a National Stage of PCT/FRO3/001919 filed Jun. 23, 2003, and claims priority to French Application Nos. 02/07763, 02/07764 and 02/07765 all filed on Jun. 21, 2002.

FIELD OF THE INVENTION

The present invention relates mainly to the use of taurine and/or hypotaurine in oral compositions for preventing and treating functional disorders of the pilosebaceous unit and especially for preventing and treating alopecia. The invention is also directed toward the use of fatty acid(s) polyphenol and/or extracts containing the same, optionally in combination with taurine in food supplements for treating and preventing these same disorders.

BACKGROUND OF THE INVENTION

Certain physiological impairments appear with age, seasonal variations, stress and atmospheric attacking factors. They include in particular a reduction in hair density during aging, the number and diameter of the hair stems decreasing. In particular, certain individuals develop alopecia.

To prevent hair impairments that appear mainly with age, use has been made hitherto of essential amino acids, which are recognized as being vital as nutrients for the synthesis of keratin in the hair bulb. Thus, methionine, cystine and cysteine are known to have a direct impact on the metabolism of the hair follicle. However, these essential amino acids act on protein synthesis, which is not the only mechanism involved in the phenomenon of alopecia.

Among the causes of alopecia, it has in fact been determined that impairment of the perifollicular connective tissue was reflected by rigidification of the connective sheath, which is thought to explain the miniaturization of the hair follicle, a sign of aging of the pilosebaceous unit.

Furthermore, these impairments in the hair are often accompanied by impairment in the condition of the scalp, such as the abundant production of sebum. Hypersecretion of sebum or seborrhea and its consequences, for example acne, often appear during puberty, but may continue into adulthood, especially in women, for hormonal reasons.

These disorders may occur in combination, to varying degrees, in the same individual.

To combat alopecia, which characterizes the hair follicle, it has been recommended to use medicinal products that inhibit collagen metabolism. It is known practice especially to use minoxidil, and, at the present time, the mechanism of action of minoxidil, which is known to be able to combat the process of miniaturization of the hair follicle, without being antiandrogenic, is still unknown.

To combat the hypersecretion of sebum, local treatments have been proposed, including isotretinoin, but this treatment is not without serious side effects.

It has also been recommended to use antiandrogens against alopecia and hypersecretion of sebum, via the systemic route. However, this type of treatment is not without serious side effects, in particular on the sexual organs.

For its part, document WO 99/22728 describes numerous compounds, including fatty acids, especially for therapeutic uses. However, the medicinal products have drawbacks associated with the risks inherent in their use, insofar as the medicinal products are xenobiotics. In addition, the medicinal products generally have a highly targeted spectrum of action, whereas the causes of impairment of the pilosebaceous unit are manifold.

Moreover, taurine is described as being a cellular activator for regulating hair cells and is proposed in hair-stimulating compositions for topical application, in document WO 02/24189. However, the taurine used as topical cellular activator has limited effect due to the fact that the loss of cellular activity may be caused by several factors of alopecia. If these factors persist, the temporary effects of a topical application of a cellular activator are limited. Furthermore, compositions for topical use have for their part drawbacks associated with local application. The frequency of the applications is generally higher and the application of these compositions to a large area to be treated may require a certain amount of time.

It has thus been found that there is still a need for active agents that can be administered orally, which are effective in the treatment and/or prevention of the signs of aging of the hair and/or functional disorders of the pilosebaceous unit, and especially alopecia, and which are free of side effects. The pilosebaceous unit comprises a hair follicle and its sebaceous gland.

BRIEF SUMMARY OF THE INVENTION

The Applicant has demonstrated, surprisingly, firstly that taurine is advantageous in regulating the impairment of the connective tissue of the hair follicle, and may thus be used advantageously in the treatment and prevention of aging of the pilosebaceous unit and/or of alopecia. Specifically, it has been possible to observe that taurine reduces the incorporation of proline without impairing that of leucine; this shows the advantage of taurine for specifically reducing the accumulation of collagen, without impairing the overall synthesis of proteins.

Moreover, the Applicant has also found that extracts rich in polyphenols and/or in fatty acids, used orally, especially as a food supplement, have beneficial activity on disorders arising in the pilosebaceous unit. Oral compositions comprising polyphenols and/or fatty acids may especially prevent the cutaneous activation of testosterone (intacrine) and the increase in sebaceous function resulting therefrom, without any general effect on the genital apparatus or the sexual functions.

Moreover, the Applicant has noted that favoring an oral administration made it possible to obtain a hair-loss-preventing effect without inducing a stimulatory effect on the growth of the pilous system other than the hair system. It thus found that an oral administration of the active materials under consideration according to the invention was particularly effective for maintaining a good head of hair by acting on the hair density, i.e. the number of hairs per $cm^2$ of scalp, and by reducing the heterogeneity of the hair diameters.

DESCRIPTION OF THE INVENTION

Figure 1:
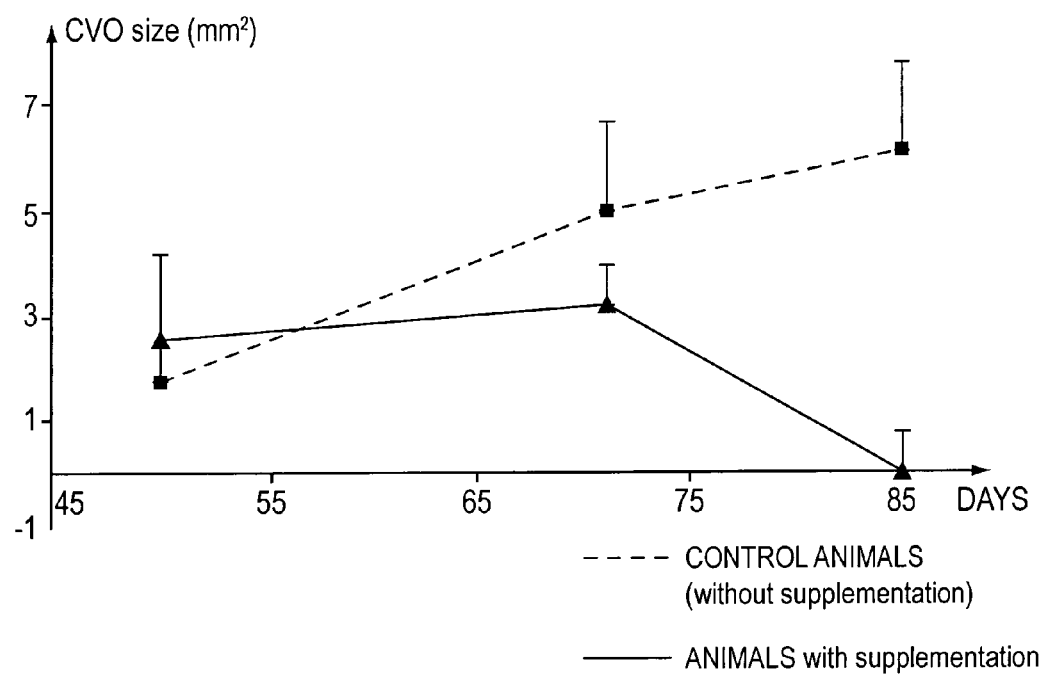
FIG. 1: This shows the results of the ingestion of fatty acids by hamsters, in a CVO test.

Thus, according to one of its aspects, the present invention relates to the use of taurine and/or hypotaurine and/or salts thereof that are acceptable in an oral composition, for the preparation of an oral composition that is useful for treating and preventing aging of the pilosebaceous unit and/or alopecia and in particular for preventing or reducing impairment of the connective tissue of the hair follicle that is especially induced by rigidification of the connective sheath.

Taurine, hypotaurine or acceptable salts thereof may be used according to the invention, in compositions for oral use, which are useful for reducing or preventing impairment of the hair follicle induced by excessive crosslinking and/or synthesis of natural collagens, for regulating the metabolism and structure of collagens in cutaneous and perifollicular tissue, and in particular in the connective sheath of the hair follicle. In particular, taurine and/or hypotaurine and/or acceptable salts thereof may be used for preventing miniaturization of the hair follicle.

According to one variant of the invention, the taurine and/or hypotaurine and/or acceptable salts thereof are used in combination with at least one of the compounds chosen from fatty acids, polyphenols and extracts comprising the same.

According to another of its aspects, the present invention is also directed toward the use of polyphenol(s) chosen from flavonols, anthocyanins, flavanols, proanthocyanidins and flavanones, and stilbenes, and/or of fatty acid(s) chosen from n-6 and n-3 essential polyunsaturated fatty acids, containing between 18 and 22 carbon atoms, and also esters thereof, and mixtures thereof, and/or of an extract comprising the same, for the preparation of an oral composition, especially a food supplement, that is useful for treating or preventing disorders of the pilosebaceous unit, in particular useful for reducing or preventing seborrhea or even for reducing or preventing hair loss.

These oral compositions are especially advantageous for reducing or preventing the excessive metabolism of androgens in the skin and/or for reducing or preventing the impact of testosterone on the pilosebaceous unit.

The present invention also relates to compositions for oral absorption comprising taurine and/or hypotaurine and/or acceptable salts thereof for oral absorption, said compositions comprising as active agent at least 0.05% to 80% by weight of taurine and/or hypotaurine and/or acceptable salts thereof and an excipient, and being free of vitamin C and also comprising, where appropriate, at least one polyphenol and/or one fatty acid and/or an acceptable salt thereof in an oral composition.

More particularly, the polyphenols are chosen from flavones, flavonols, isoflavones, anthocyanins, flavanols, proanthocyanidins and flavanones, and stilbenes, and the fatty acids are chosen from n-6 and n-3 essential polyunsaturated fatty acids, containing between 18 and 22 carbon atoms, and also esters thereof, and mixtures thereof.

Another aspect of the invention relates to a composition for oral absorption comprising at least one polyphenol chosen from flavonols, anthocyanins, flavanols, proanthocyanidins and flavanones and stilbenes and/or a fatty acid chosen from n-6 and n-3 essential polyunsaturated fatty acid(s), containing between 18 and 22 carbon atoms, and also esters thereof, and mixtures thereof, and/or an extract comprising the same, in combination with taurine and/or hypotaurine and/or acceptable salts thereof for oral absorption and, where appropriate, an excipient.

The compositions for oral absorption according to the invention may comprise 0.01% to 30% by weight of taurine and/or hypotaurine and/or acceptable salts thereof, in combination with 0.1% to 50% by weight of extracts comprising at least one polyphenol, and especially with 0.1% to 25% by weight, especially 0.1% to 20% by weight or even 0.1% to 15% by weight of catechins.

The compositions for oral absorption according to the invention may especially contain taurine and/or hypotaurine and/or acceptable salts thereof, in combination with polyphenols in a polyphenol/taurine weight ratio at least equal to 0.5, in particular greater than or equal to 0.75 and especially greater than or equal to 1.

Another aspect of the invention relates to a composition for oral absorption comprising at least 0.01% to 30% by weight of taurine and/or hypotaurine and/or acceptable salts thereof, in combination with 0.01% to 10% by weight of fatty acids.

According to one particular embodiment, the oral compositions of the invention are food supplements.

The present invention is moreover directed toward a cosmetic process for treating and preventing aging of the hair and/or alopecia via the oral administration of taurine and/or hypotaurine and/or salts acceptable for oral administration.

According to another of its aspects, the invention relates to a cosmetic process for treating and preventing disorders of the pilosebaceous unit via the oral administration of at least one fatty acid, one polyphenol or an extract comprising the same, optionally in combination with taurine and/or hypotaurine and/or acceptable salts thereof.

In one particular embodiment, the taurine, hypotaurine or acceptable salts thereof is (are) administered at a dose of from 0.5 to 4000 mg per day, as taurine equivalent, the fatty acid(s) is (are) administered at a dose of from 0.5 to 5400 mg/day and/or the polyphenol(s) is (are) administered at a dose of from 0.5 to 2000 mg/day.

According to the invention, the expected effects are achieved without the adverse effects of a medicinal product, inexpensively compared with the price of a treatment with a medicinal product. The oral intake of the active agent(s) allows a more constant effect, without it being necessary to repeat the applications.

More particularly, the efficacy limitations are lifted when this oral intake occurs in the case of individuals in whom has been detected a precursor sign of functional disorder of the pilosebaceous unit, especially alopecia, for instance a state of excessive crosslinking of the perifollicular connective tissue, for example via histology or macrophotography of the scalp.

The invention will be understood more clearly on reading the detailed description and the examples that follow.

Taurine and Hypotaurine

Taurine and/or hypotaurine, which is a metabolite thereof, may be used as active agent(s) according to the invention. It is also possible to use salts thereof that are acceptable in such oral compositions. Since the compositions according to the invention are intended to be administered to an individual, these salts are obviously chosen for their total harmlessness. In this respect, alkali metal or alkaline-earth-metal salts, in particular magnesium, manganese, iron II or zinc salts, are most particularly suitable for the invention.

According to the invention, hypotaurine, or taurine, is used in daily doses ranging from 0.5 to 4000 mg per day and preferably 10 to 500 mg per day. The daily dose is more preferably from about 50 to 150 mg per day. The doses indicated in the present description are doses as taurine equivalent.

Polyphenols

Any food-grade polyphenol may be used as polyphenol according to the invention. These compounds are generally derived from plants, and their structures are classified according to the nature of the hydrocarbon-based skeleton (Laura Bravo Nutrition Review 1998 56 pp. 317-333, Scalbert A. Williamson G, J. Nutr. 2000 130 2073s 2085S).

According to the invention, the term "polyphenols" more particularly means compounds of flavonoid type, i.e. flavones, flavonols, isoflavones, anthocyanins, flavanols, proanthocyanidins and flavanones, and stilbenes.

Flavonols, anthocyanins, flavanols, proanthocyanidins and flavanones, and stilbenes, are more particularly suitable.

The main flavanols are chosen from catechins and gallocatechins. Procyanidins are flavonol polymers present in the form of low-degree polymer mixtures. They may be associated with catechins in the plant extracts.

Polyphenols or polyphenol mixtures chosen from catechin, epicatechin, epigallocatechin 3-O-gallate, epigallocatechin, epicatechin 3-gallate, procyanidins and proanthocyanidins, and mixtures thereof, are preferably used.

It is particularly advantageous to use catechin monomers as a mixture, where appropriate, with procyanidin oligomers (PCO). Thus, the polyphenols used according to the invention cannot consist solely of catechin monomers.

These provisions of polyphenols may be made from isolated compounds and/or from plant extracts, and mixtures thereof.

According to the invention, plant extracts that can provide all of these polyphenols may be used.

More particularly, the catechins are very abundant in tea (*Camellia sinensis*) and grape (*Vitis vinifera*) and other fruit (apple, pear or pine cone (*Pinus maritima*)). Beverages (wine, beer, tea) and chocolate (*Theobroma cacao*) are sources that can constitute provisions of catechins according to the invention.

These polyphenols may be used alone or used in the form of mixtures, and may be ingested in various forms of nutritional supplements (sugarcoated tablets, gels, soluble powders, gel capsules, wafer capsules, enriched foods, etc.).

These dietary polyphenols may be used at doses of from 0.5 to 2000 mg/day, especially from 0.5 to 1000 mg/day and preferably from 20 to 300 mg/day.

In particular, these polyphenols may be administered orally in "nutritional" doses, i.e. doses equivalent to the doses absorbed by a person on a balanced diet.

By way of example, mention may be made of an extract of grapeseed containing 40% PCO, an extract of red wine containing 30% total polyphenols and/or an extract of green tea containing 30% catechins.

The procyanidin oligomers (PCO) may be used at doses of from 0.5 to 1000 mg/day and preferably 20 to 250 mg/day. They may be provided by an extract of grapeseed, which is dosed according to its PCO content. By way of example, for an extract of grapeseed containing 40% PCO, above, a dose of 150 mg/day, i.e. 60 mg/day PCO, is used.

Moreover, the catechins may be used at doses of from 0.5 to 1000 mg/day and preferably 20 to 300 mg/day. They may be provided, for example, by an extract of green tea containing 30% catechins, the extracted dose then being about 375 mg/day, i.e. 112.5 mg/day of catechins.

As examples of daily doses of polyphenols, mention may be made of daily doses of an extract of red wine rich in polyphenolic components (600 mg of powdered extract of red wine: 12 mg PCO/person/day, i.e. 18 mg total polyphenols), daily doses of an extract of grapeseed rich in polyphenolic components (300 mg of powdered extract of red wine: 18 mg PCO/person/day, i.e. 27 mg total polyphenols), daily doses of an extract of green tea rich in polyphenolic components (225 mg of powdered extract of green tea: 67.5 mg of catechins/day).

The polyphenols may be chosen from one of the above categories, and mixtures may also be used. The compositions of food supplements may comprise 0.01% to 10% by weight of at least one polyphenol.

In the case where these polyphenols are administered in combination with taurine and/or hypotaurine, they may be administered in a proportion of 0.1% to 50% by weight per 0.01% to 30% by weight of taurine and/or hypotaurine and/or acceptable salts thereof.

The Applicant has especially demonstrated that the oral administration of a dose of 37 mg/kg/day of a red wine concentrate, which is equivalent to a dose of 220 mg/kg/day for a person weighing 60 kg, had an efficacious effect on hair loss without showing any adverse side effects on the prostate. This is especially illustrated in the examples below.

As stated previously, it is advantageous to use the polyphenols in combination with taurine in a polyphenol/taurine weight ratio at least equal to 0.5, in particular greater than or equal to 0.75 and especially greater than or equal to 1. More particularly, this weight ratio may range from 0.5 to 2, especially from 0.75 to 1.5 or even from 0.9 to 1.3, and may in particular be about 1.2.

Compositions in accordance with the invention comprising from 0.01% to 30% by weight of taurine and/or hypotaurine and/or acceptable salts thereof, and especially of taurine, in combination with 0.1% to 25% by weight of catechins, especially 0.1% to 20% by weight of catechins present in the form of a plant extract or a mixture of plant extracts, are also found to be most particularly advantageous.

In the particular case of catechins, these compounds may be combined with taurine, hypotaurine and/or salts thereof in a catechin/taurine weight ratio at least equal to 0.4, especially greater than 0.7, or even between 0.7 and 1.5.

Fatty Acids

According to the invention, "fatty acids" refers to polyunsaturated fatty acids, i.e. any fatty acid containing cis,cis-methylene interrupted double bonds.

The dietary polyunsaturated fatty acids are defined according to the length of the carbon chain and the position of the double bond. The essential fatty acids are currently organized into two groups (ω3 and ω6) characterized by the position of the unsaturation closest to the terminal methyl group.

The fatty acids of two families of essential polyunsaturated fatty acids of the n-6 and n-3 fatty acid families, containing between 18 and 22 carbon atoms, and also esters thereof and mixtures thereof, are most particularly suitable for the invention. These fatty acids specifically have the advantage of being permitted according to the food standards.

Preferably, these fatty acids are not associated with terpenes or terpene derivatives.

For the polyunsaturated fatty acids of the n-6 series, known as "omega-6" fatty acids, mention may be made of the first, linoleic acid, containing 18 carbon atoms and two unsaturations: (18:2ω6), and γ-linolenic acid (18:3ω6) is also a fatty acid that is particularly advantageous according to the invention.

The sources of γ-linolenic acid will be chosen from plant oils (evening primrose oil, borage oil, blackcurrant pip oil and hemp oil), and extracts of *spirulina, Spirula maxima* and *S. platensis*.

For the polyunsaturated fatty acids of the n-3 series, known as "omega-3" polyunsaturated fatty acids, the first is alpha-linolenic acid (18:3ω3); stearidonic acid (C18:4n-3) is also a fatty acid that is particularly advantageous in the invention.

Plant oils from walnut (*Juglans regia*) and from soybean (*Glycina max*), for example, are rich in omega-3 polyunsaturated fatty acids in the same respect as fish oils.

The ω3 polyunsaturated fatty acids are found, via the food chain, in zooplankton, crustaceans/molluscs and fish.

Fish oils constitute the main industrial source of EPA (eicosapentaenoic acid=20:5 ω3) and DHA (docosahexaenoic acid=22:6 ω3). However, microalgal biomasses may also constitute a raw material for extraction of ω3 fatty acids.

The nutritional quality of the microalgae may be improved by means of a judicial choice of strains and by a metabolic orientation associated with the culture conditions.

The advantage of microalgae is all the greater since they synthesize fatty acids such as EPA and DHA.

Preferably, linoleic acid, γ-linolenic acid, linolenic acid, stearidonic acid, crocetin and 5,8,11,14-eicosatetraenoic acid and mixtures thereof or extracts comprising them are used. Thus, the fatty acid(s) and/or the extract(s) may be used alone or as mixtures.

The recommended daily doses according to the invention are, for the fatty acids, between 0.5 and 3500 mg/day and especially between 5 and 1500 mg/day.

The recommended daily doses according to the invention are, for the n-3 fatty acids, between 0.5 and 2500 mg/day and preferably 5 to 360 mg/day, and, for the n-6 fatty acids, between 0.5 and 2600 mg/day and preferably 5 to 1200 mg/day.

The fatty acids may be chosen from one of the above categories, and mixtures thereof may also be used. The oral compositions may comprise 0.01% to 10% by weight of at least one fatty acid.

In the case of a combination with taurine and/or hypotaurine and/or acceptable salts thereof, the compositions according to the invention may comprise from 0.01% to 30% by weight of taurine and/or hypotaurine and/or acceptable salts thereof with 0.01% to 10% by weight of fatty acids.

Other Active Agent(s)

The active agents under consideration according to the invention, namely taurine, hypotaurine or salts thereof, fatty acids, polyphenols and mixtures thereof, may be combined with one or more other active agents such as, especially, vitamins and antioxidants, optionally in the form of complexes.

For the purposes of the present invention, the term "active agent" means that the compound under consideration, for example taurine, is used to manifest the biological and chemical activity intrinsic thereto rather than for a function of vehicle or excipient type.

Needless to say, the compositions according to the invention may contain several active agents.

As active agents that may be used, mention may be made of zinc and its salts, especially the sulfate and gluconate, vitamins B5, B6, B8, C, E or PP, β-carotene and carotenoids, garlic extracts in the form of allyl sulfide or ajoene for example, selenium, curcumin, curcuminoids, niacin, lithospermic acid and adenosine.

In particular, an antioxidant complex comprising vitamins C and E, zinc or salts thereof, selenium and at least one carotenoid, especially a carotenoid chosen from β-carotene, lycopene, zeaxanthin and lutein, may be used.

An antioxidant complex comprising, for example, from 100 to 150 mg of vitamin C per 80 to 120 μg of selenium, 20 to 50 mg of vitamin E, 10 to 40 mg of zinc and 3 to 10 mg of β-carotene is preferred.

However, the compositions according to the invention may advantageously contain less than 1% by weight of vitamin C, or may even be free of vitamin C.

The active agents according to the invention may also be combined with known hair-loss-preventing active agents, and especially compounds that further enhance their activity toward regrowth of the hair and/or stopping hair loss, such as, more particularly, the following compounds:

nicotinic acid esters, more particularly including $C_3$-$C_6$ alkyl nicotinates and especially methyl or hexyl nicotinate, benzyl nicotinate or tocopheryl nicotinate;

steroidal and nonsteroidal antiinflammatory agents that are well known in the state of the art, and in particular hydrocortisone and its salts and derivatives, and niflumic acid;

retinoids and more particularly t-trans-retinoic acid, also known as tretinoin, isotretinoin, retinol or vitamin A and its derivatives, such as the acetate, palmitate or propionate, motretinide, etretinate and zinc trans-retinoate;

antibacterial agents more particularly chosen from macrolides, pyranosides and tetracyclines, and especially erythromycin;

calcium antagonists such as Cinnarizine and Diltiazem;

hormones such as estriol or analogs, or thyroxine and its salts;

antiandrogenic agents such as oxendolone, spironolactone or diethylstilbestrol;

OH-radical scavengers such as dimethyl sulfoxide;

esterified oligosaccharides such as those described in EP-A-0 211 610 and EP-A-0 064 012;

hexosaccharidic acid derivatives such as those described in EP-A-0 375 388, in particular glucosaccharidic acid;

glycosidase inhibitors such as those described in EP-A-0 334 586, in particular D-glucaro-1,5-lactam;

glycosaminoglycanase and proteoglycanase inhibitors such as those mentioned in EP-A-0 277 428, in particular L-galactono-1,4-lactone;

tyrosine kinase inhibitors such as those described in EP-A-0 403 238, in particular 1-amido-1-cyano-(3,4-dihydroxyphenyl)ethylene.

The active agents of the invention may also be combined with, optionally as a mixture with the others, compounds such as Diazoxide corresponding to 3-methyl-7-chloro[2H]-1,2,4-benzothiadiazine 1,1-dioxide; Spiroxazone or 7-(acetylthio)-4',5'-dihydrospiro[androst-4-ene-17,2'-(3'H)furan]-3-one; phospholipids such as lecithin; salicylic acid and its derivatives described more particularly in French patent No. 2 581 542, and more particularly salicylic acid derivatives bearing an alkyl group containing from 2 to 12 carbon atoms in position 5 of the benzene ring, hydroxycarboxylic or keto carboxylic acids and esters thereof, lactones and the corresponding salts thereof; anthralin, eicosa-5,8,11-triynoic acids, esters and amides thereof, and minoxidil and its derivatives, which are compounds described in EP 353 123, EP 356 271, EP 408 442, EP 522 964, EP 420 707, EP 459 890, EP 519 819, U.S. Pat. No. 4,139,619 and U.S. Pat. No. 459,812.

The above compounds are incorporated into the oral compositions and especially the food supplements provided that their use as food supplement is possible, and their formulation compatible with that of the active agents of the invention. These additional active agents are used according to the invention at doses that are compatible with their use as food supplements. Thus, for certain compounds, it will be preferred to use them topically, as a supplement to the food supplements of the invention.

For the ingestion of the active agent(s), numerous embodiments of oral compositions and especially of food supplements are possible. They are formulated via the usual processes for producing sugarcoated tablets, gel capsules, gels, emulsions, tablets, wafer capsules or liquid solutions, especially drinkable ampules, for example. In particular, the active agent(s) according to the invention may be incorporated into any other form of food supplements or of enriched foods, for example dietary bars, or compacted or noncompacted powders. The powders may be dilutable in water, in soda, dairy products or soybean derivatives, or may be incorporated into dietary bars.

The active agents may be formulated with the common excipients and components for such oral compositions or food supplements, such as, especially, fatty and/or aqueous components, humectants, thickeners, preserving agents, texture, taste and/or coating agents, antioxidants, preserving agents and dyes that are common in the food sector.

The formulating agents and excipients for oral compositions, and especially for food supplements, are known in this field and will not be described in detail.

The cosmetic process according to the invention is performed by means of an oral intake, for example daily, of an oral composition or food supplement, which may be, for example, in the form of gel capsules, gels, sugarcoated tablets, emulsions, tablets, wafer capsules or drinkable ampules, in adequate amount and number, depending on their form, such that the taurine and/or hypotaurine or acceptable salts thereof are ingested in a proportion of from 0.5 to 4000 mg per day, preferably 10 to 500 mg per day and more preferably about 150 mg per day, as taurine equivalent, and/or such that the polyphenol(s) is (are) ingested at doses of about from 0.5 to 2000 mg/day, and/or such that the fatty acids are ingested at doses of from 0.5 to 5400 mg per day and preferably from 5 to 1600 mg per day.

The process according to the invention may consist of a single intake, but is generally applied over a prolonged period of at least 4 weeks, or even 4 to 8 weeks, with, where appropriate, one or more periods of interruption.

By way of example, for γ-linolenic acid, which may be provided by blackcurrant pip oil, doses of about from 10 to 3000 mg/day and preferably from 50 to 1000 mg/day may be envisioned.

In the description and in the examples that follow, unless otherwise mentioned, the percentages are weight percentages and the ranges of values mentioned in the form "between . . . and . . . " include the lower and upper limits mentioned. The ingredients are mixed, before being fashioned, in the order and under conditions that are readily implemented by a person skilled in the art.

The examples and figures given below are presented as nonlimiting illustrations of the field of the invention.

FIG. 1: This shows the results of the ingestion of fatty acids by hamsters, in a CVO test.

Figure 2:
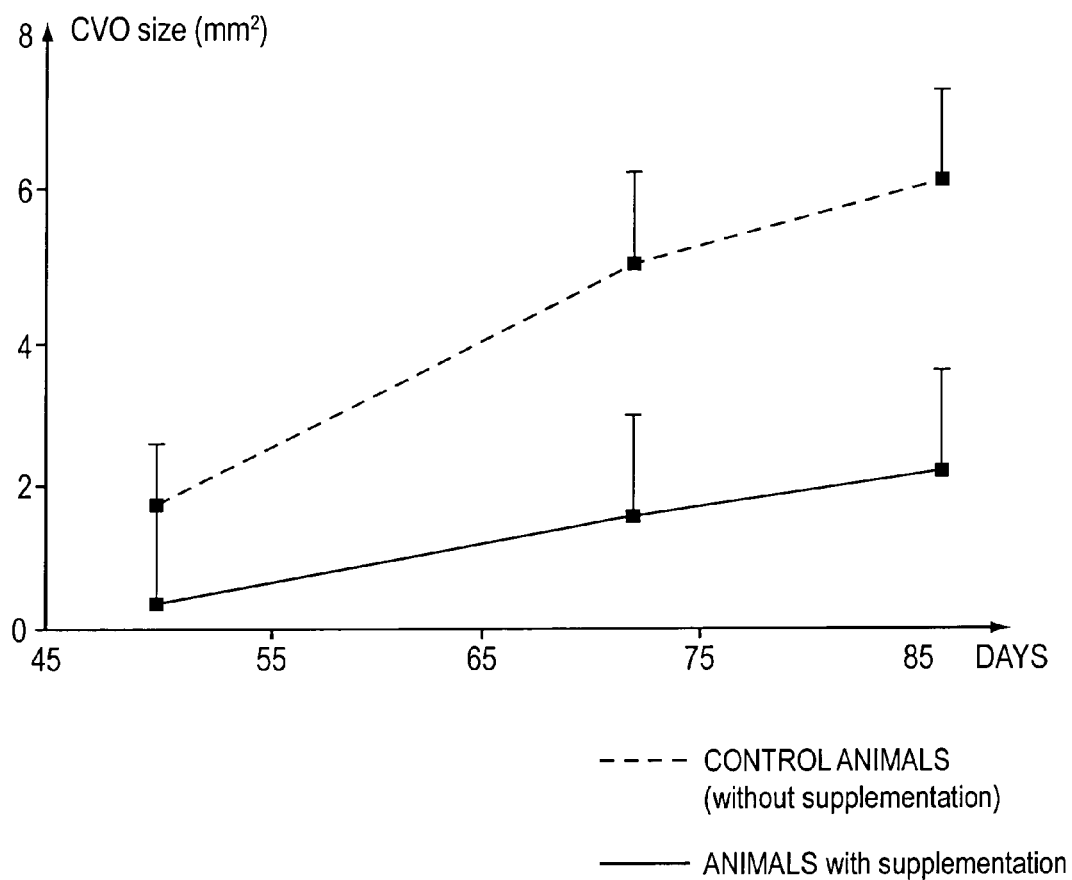
FIG. 2: This shows the results of the ingestion of polyphenols by hamsters in a CVO test.

FIG. 2: This shows the results of the ingestion of polyphenols by hamsters in a CVO test.

Figure 3:
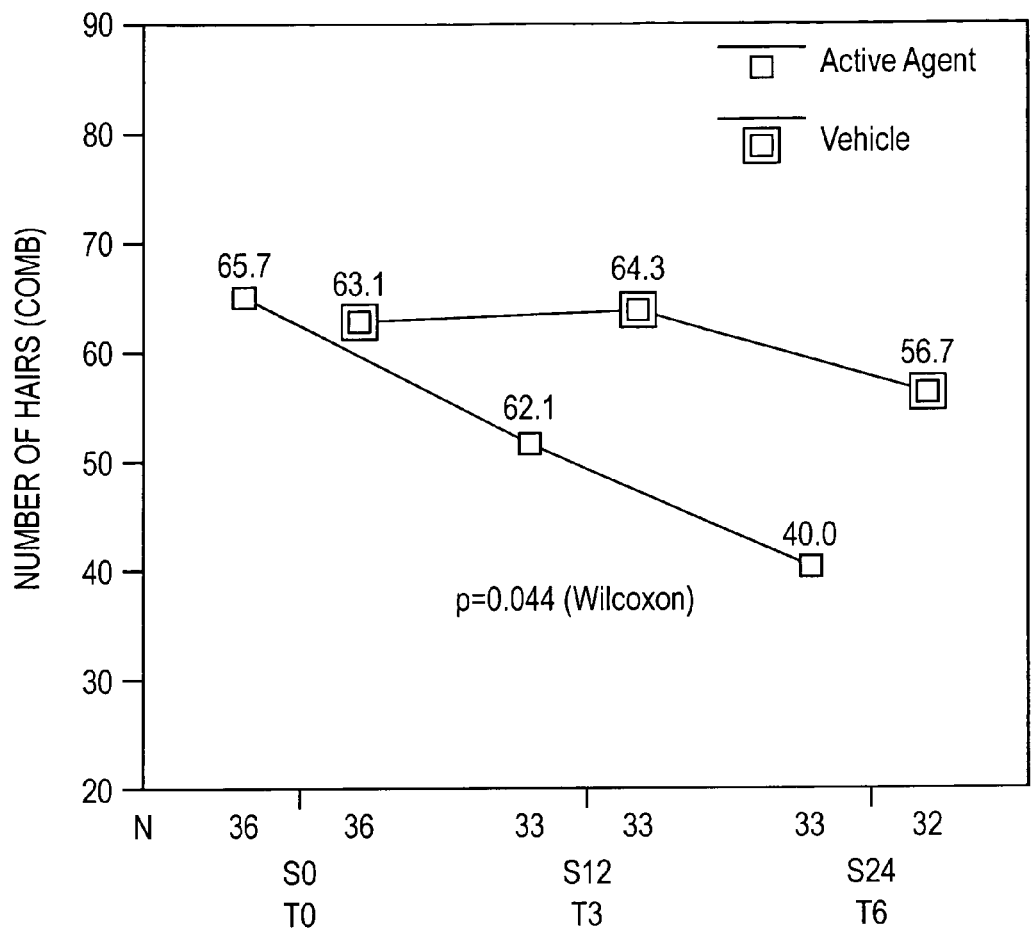
FIG. 3: This shows the results of hair-loss prevention found in the case of individuals treated according to the invention and of control individuals.

FIG. 3: This shows the results of hair-loss prevention found in the case of individuals treated according to the invention and of control individuals.

EXAMPLE TO DEMONSTRATE THE ACTIVITY OF FATTY ACIDS AND POLYPHENOLS

In order to demonstrate the activity of these compounds, a test of detection of activity on a specific pilosebaceous formation was used: the CVO test.

The hamster CVO (costovertebral organ) is a cutaneous region rich in pilosebaceous units (hair follicles and the sebaceous glands thereof). The size of this formation is increased under the action of testosterone. The test (Liao S. & al. Arch Dermatot Res 2001 April: 293(4): 200-205) consists in determining the antiandrogenic action of compounds on the CVO, i.e. in determining whether the compounds prevent the action of testosterone.

1/CVO Test with Fatty Acids

In this test, blackcurrant pip oil at 10% in feed is given to male hamsters for 85 days. It is found that this nutritional supplement prevents the testosterone-induced increase in the size of the CVO.

Thus, in FIG. 1, the dashed curve represents the change in the size of the CVO ($mm^2$) in control animals, without supplementation, during the experiment (days on the x-axis): there is a testosterone-induced increase in the size of the CVO. The solid-line curve shows the change in the size of the CVO in the case of animals with supplementation: this increase is reduced to virtually zero.

2/CVO Test with Polyphenols

Hamsters were fed a nutrient in the form of Robertet red wine concentrate comprising 18% of flavanoid components (0.11 g in 43 g of feed) daily, and it was found that the right CVO/left CVO difference was virtually zero, at 85 days of ingestion (FIG. 2).

Thus, in FIG. 2, the dashed curve shows the change in the size of the CVO ($mm^2$) in the case of control animals, without supplementation, during the experiment (days on the x-axis): there is a testosterone-induced increase in the size of the CVO. The solid-line curve shows the change in the size of the CVO in the case of animals with supplementation: this increase is reduced to virtually zero.

3/Absence of Sexual Side Effect

In the case of the hamsters that received these oral nutritional supplements, a repercussion of the anti-androgenic action was found not only on the CVO, but also on the sexual organs in the case of male animals. In both cases, it was found that these nutritional supplements did not impair the weight of the seminal vesicles or of the prostate.

Example to Demonstrate the Activity of Taurine

A study was performed with the aim of evaluating, via a screening method, the effects of the compounds on the growth of fibroblasts and the synthesis of the major constituents of the extracellular matrix. The technique made it possible to study and evaluate the advantage of taurine on this cell metabolism (T. Shigematsu et al. Biochimica et Biophysica Acta 1200 (1994) 79-83).

A pool of normal human dermal fibroblasts (NHDF pool PF2, used at the eighth passage) was cultured under standard conditions in a medium: DMEM, 2 mM L-glutamine, 50 IU/ml/50 g/ml penicillin/streptomycin, 0.5% fetal calf serum.

Taurine was tested at concentrations of 10 mM and 1 mM in a sterile culture medium, against an untreated control blank.

The results of the incorporation of thymidine, proline and leucine into the fibroblasts are given in table I below, which shows the effect of taurine on the incorporation of thymidine, proline and leucine in macromolecules neosynthesized by the NHDFs in in vitro culture. The figures in bold are those for which there is a significant variation (stat. sign. meaning statistical significance: $p<0.005$). The results are expressed as a percentage of the control.

TABLE 1

|  | Thymidine | | Proline | | Leucine | |
| --- | --- | --- | --- | --- | --- | --- |
|  | % control | Stat. sign. | % control | Stat. sign. | % control | Stat. sign. |
| 1 mM taurine | 89 | p > 0.05 | 88 | p < 0.01 | 100 | p > 0.05 |
| 10 mM taurine | 90 | p > 0.05 | 87 | p < 0.01 | 105 | p > 0.05 |

It is seen that taurine, at the two treated concentrations, did not significantly modify the incorporation of thymidine, which is representative of the cell proliferation, or of leucine, which is representative of the synthesis of noncollagen protein, by the fibroblasts; on the other hand, taurine did significantly inhibit the incorporation of proline by the fibroblasts.

FORMULATION EXAMPLES

Example 1

| FORMULATION OF SUGARCOATED TABLET TYPE | |
|---|---|
| | mg/sugarcoated tablet |
| Taurine | 50 |
| Excipient for the core of the sugarcoated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

This type of sugarcoated tablet may be taken 2 to 3 times a day.

Example 2

| PLANT OR ANIMAL GELATIN GEL CAPSULE | |
|---|---|
| Active principle | mg/sugarcoated tablet |
| Taurine | 80 |
| Starch | 128 |
| Magnesium stearate | 2.5 |

This type of gel capsule may be taken two or three times a day.

Example 3

| SINGLE-DOSE GEL | |
|---|---|
| | wt % |
| Active principle | |
| Taurine | 4 |
| Zinc-enriched yeast (22.75% Zn) | 2 |
| Excipient | |
| Rhodigel ™ | 2.3 |
| Cocoa extract | 20 |
| Potassium sorbate | 0.05 |
| Sodium benzoate | 0.05 |
| Water | qs 100 |

200 to 400 ml of this product may be used per day.

Example 4

| SINGLE-DOSE GEL | |
|---|---|
| | wt % |
| Active principle | |
| Taurine | 4 |
| Blackcurrant pip oil | 10 |
| Excipient | |
| Sugar syrup | 50 |
| Maltodextrin | 17 |
| Xanthan gum | 0.8 |
| Sodium benzoate | 0.2 |
| Water | qs 100 |

200 to 400 ml of this product may be used per day.

Example 5

| SINGLE-DOSE GEL | |
|---|---|
| | wt % |
| Active principle | |
| Taurine | 4 |
| Blackcurrant pip oil | 10 |
| Antioxidant complex | * |
| Excipient | |
| Sugar syrup | 50 |
| Maltodextrin | 17 |
| Xanthan gum | 0.8 |
| Sodium benzoate | 0.2 |
| Water | qs 100 |

* The antioxidant complex comprises 120 mg of vitamin C, 100 µg of selenium, 30 mg of vitamin E, 20 mg of zinc and 6 mg of β-carotene per 200 ml of gel.

200 to 400 ml of this product may be used per day.

Example 6

| WAFER CAPSULE | |
|---|---|
| | mg/capsule |
| Taurine | 50 |
| Zinc gluconate | 160 |
| Wine extract (20% PCO) | 300 |
| Glycerol | 150 |
| Magnesium stearate | 0.02 |
| Water | qs 900 mg |

Example 7

| WAFER CAPSULE | |
|---|---|
| | mg/capsule |
| Taurine | 50 |
| Zinc gluconate | 160 |

-continued

WAFER CAPSULE

|  | mg/capsule |
| --- | --- |
| Wine extract (20% PCO) | 300 |
| Glycerol | 150 |
| Magnesium stearate | 0.02 |
| Vitamin complex | qs* |
| Water | qs 900 mg |

*The vitamin complex comprises 60 mg of vitamin C, 50 µg of selenium, 15 mg of vitamin E, 10 mg of zinc and 3 mg of lycopene.

Example 8

FORMULATION OF SUGARCOATED TABLET TYPE

|  | mg/sugarcoated tablet |
| --- | --- |
| Taurine | 50 |
| Grapeseed extracts (40% PCO) | 100 |
| Green tea extracts (30% catechins) | 125 |
| Zinc sulfate (22.75%) | 22 |
| Excipient for the core of the sugarcoated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

This type of sugarcoated tablet may be taken 1 to 3 times a day.

Example 9

FORMULATION OF SUGARCOATED TABLET TYPE

|  | mg/sugarcoated tablet |
| --- | --- |
| Grapeseed extracts (40% PCO) | 100 |
| Green tea extracts (30% catechins) | 125 |
| Zinc sulfate (22.75%) | 22 |
| Excipient for the core of the sugarcoated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

This type of sugarcoated tablet may be taken once or twice a day.

Example 10

FORMULATION OF SUGARCOATED TABLET TYPE

|  | mg/sugarcoated tablet |
| --- | --- |
| Taurine | 50 |
| Grapeseed extracts (40% PCO) | 50 |
| Green tea extracts (30% catechins) | 125 |
| Zinc sulfate (22.75%) | 22 |
| Excipient for the core of the sugarcoated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

This type of sugarcoated tablet may be taken 1 to 3 times a day.

Example 11

PLANT OR ANIMAL GELATIN GEL CAPSULE

| Active principle | mg/gel capsule |
| --- | --- |
| Grapeseed extract (40% PCO) | 50 |
| Green tea extract (30% catechins) | 175 |
| Starch | 128 |
| Magnesium stearate | 2.5 |

One to four gel capsules may be taken per day.

Example 12

PLANT OR ANIMAL GELATIN GEL CAPSULE

| Active principle | mg/gel capsule |
| --- | --- |
| Taurine | 80 |
| Grapeseed extract (40% PCO) | 50 |
| Green tea extract (30% catechins) | 175 |
| Starch | 128 |
| Magnesium stearate | 2.5 |

One to four gel capsules may be taken per day.

Example 13

| SINGLE-DOSE GEL | |
|---|---|
| | wt % |
| Active principle | |
| Taurine | 4 |
| Grapeseed extract (40% PCO) | 4 |
| Green tea extract (30% catechins) | 6 |
| Zinc-enriched yeast (22.75% Zn) | 2 |
| Excipient | |
| Rhodigel ™ | 2.3 |
| Cocoa extract | 20 |
| Potassium sorbate | 0.05 |
| Sodium benzoate | 0.05 |
| Water | qs 100 |

200 to 400 ml of gel are taken per day.

Example 14

| SINGLE-DOSE GEL | |
|---|---|
| | wt % |
| Active principle | |
| Grapeseed extract (40% PCO) | 4 |
| Green tea extract (30% catechins) | 10 |
| Blackcurrant pip oil | 10 |
| Excipient | |
| Sugar syrup | 50 |
| Maltodextrin | 17 |
| Xanthan gum | 0.8 |
| Sodium benzoate | 0.2 |
| Water | qs 100 |

200 to 400 ml of gel are taken per day.

Example 15

| WAFER CAPSULE | |
|---|---|
| | mg/capsule |
| Taurine | 50 |
| Zinc gluconate | 60 |
| Wine extract (20% PCO) | 300 |
| Glycerol | 150 |
| Magnesium stearate | 0.02 |
| Water | qs 900 mg |

One to four wafer capsules are taken per day.

Example 16

Powders

A 1.8 g wine extract providing up to 540 mg of total polyphenols (including 360 mg of PCO), up to 120 mg of taurine, 0.01 g of Goldblend sweetener, 0.4 g of FRAM0584 flavoring and 4 g of maltodextrin was used in the form of a powder to be diluted in water, in a dairy product or incorporated into a cereal/fruit dietary bar to be consumed each day.

Under the same conditions, the following were used:

A mixture of extracts of *Vitis vinifera* and/or of a biotechnological product thereof (grape juice, wine, etc.) providing the same amount of total polyphenols in combination with a source of taurine-rich natural proteins providing an amount of taurine of 150 mg/day.

An extract of *Camellia sinensis* or of *Theobroma cacao* providing the same amount of total polyphenols, in combination with a source of taurine-rich natural proteins providing the same amount of taurine.

Example 17

A vitamin complex comprising 120 mg of vitamin C, 100 µg of vitamin E, 20 mg of zinc and 6 mg of β-carotene, in 200 ml of gel from example 5 and 60 mg of vitamin C, 50 µg of vitamin E, 10 mg of zinc and 3 mg of β-carotene in a sugar-coated tablet of example 10 is added to the gel formulation of example 13.

Example 18

In the formulations of example 17, the β-carotene is replaced with lycopene.

Example 19

| SINGLE-DOSE GEL | |
|---|---|
| | wt % |
| Active principle | |
| Taurine | 4 |
| Grapeseed extracts (40% PCO) | 4 |
| Green tea extract (30% catechins) | 6 |
| Blackcurrant pip oil | 10 |
| Excipient | |
| Sugar syrup | 50 |
| Maltodextrin | 17 |
| Xanthan gum | 0.8 |
| Sodium benzoate | 0.2 |
| Water | qs 100 |

A dose of 200 to 400 ml may be taken per day.

Example 20

| WAFER CAPSULE | |
|---|---|
| | mg/capsule |
| Taurine | 50 |
| Zinc gluconate | 60 |
| Wine extract (20% PCO) | 200 |
| Blackcurrant pip oil | 300 |
| Glycerol | 150 |
| Magnesium stearate | 0.02 |
| Natural flavoring | |
| Water | qs 900 mg |

One to three of these wafer capsules may be taken per day.

Example 21

| FORMULATION OF SUGARCOATED TABLET TYPE | |
|---|---|
| | mg/sugarcoated tablet |
| Taurine | 50 |
| Grapeseed extracts (40% PCO) | 50 |
| Green tea extracts (30% catechins) | 125 |
| Zinc sulfate (22.75%) | 22 |
| Excipient for the core of the sugarcoated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Colorant | 5 |

This type of sugarcoated tablet may be taken 1 to 3 times a day.

Example 22

A vitamin complex comprising 120 mg of vitamin C, 100 μg of vitamin E, 20 mg of zinc and 6 mg of β-carotene, per 200 ml of gel, is added to the formulation of example 19.

Example 23

A vitamin complex comprising 120 mg of vitamin C, 100 μg of vitamin E, 20 mg of zinc and 6 mg of lycopene, per 200 ml of gel, is added to the formulation of example 19.

Example 24

A vitamin complex comprising 60 mg of vitamin C, 50 μg of vitamin E, 10 mg of zinc and 3 mg of lycopene, for a sugarcoated tablet, is added to the formulation of example 22.

Example 25

| FORMULATION OF TABLET TYPE | |
|---|---|
| Active principle | Mg/tablet |
| Taurine | 75 |
| Grapeseed extracts (40% PCO) | 75 |
| Green tea extracts (30% catechins) | 187.5 |
| Zinc gluconate (14.3% zinc) | 52.3 |
| Excipient | qs 1 g |

This type of tablet is taken twice a day.

Example 26

Two groups of 36 women from 18 to 40 years old approximately, having fine, lifeless and seborrheic hair, took for six months:
either the hair formulation having the following composition:

| | mg |
|---|---|
| Taurine | 150 |
| Green tea extract (30% catechins) | 375 |
| Grapeseed extract (40% PCO and 20% catechins) | 150 |
| Zinc sulfate (22.75%) | 15* |

*expressed as weight of zinc or a placebo, a maltodextrin-based tablet of identical appearance.

The effect of the treatment was examined by self-evaluation, and by casting a comb through the hair three times at T0, T3 months and T6 months.

A uniform decrease in the number of hairs on the comb was noted in the treated group, this difference being statistically significant, compared with the group at six months which received the placebo. The results are given in FIG. 3.

The invention claimed is:

1. A method of treating miniaturization of the hair follicle, comprising administering to a human being an oral composition comprising at least one of taurine, hypotaurine, salts of taurine and salts of hypotaurine, and at least one polyphenol, said polyphenol being selected from the group consisting of procyanidins, proanthocyanidins, a mixture of catechin monomers with procyanidin oligomers, and mixtures thereof, a weight ratio of polyphenol/taurine being at least 0.5, in an amount effective for treating miniaturization of the hair follicle;
wherein the taurine, hypotaurine, and salts thereof are the sole active amino acid.

2. The method as claimed in claim 1, wherein the method treats impairment of the connective tissue of the hair follicle.

3. The method as claimed in claim 1, wherein the method treats impairment of the hair follicle induced by rigidification of the connective sheath.

4. The method as claimed in claim 1, wherein the method treats impairment of the hair follicle induced by excessive crosslinking and/or synthesis of natural collagens.

5. The method as claimed in claim 1, wherein the method regulates the metabolism and structure of collagens in perifollicular skin tissue.

6. The method as claimed in claim 1, wherein the method regulates the metabolism and structure of collagens in the connective sheath of the hair follicle.

7. The method as claimed in claim 1, wherein an amount of taurine is between 0.5 and 4000 mg/day in the form of taurine and/or hypotaurine and/or salts thereof.

8. The method as claimed in claim 1, wherein an amount of taurine is between 10 and 500 mg/day in the form of taurine and/or hypotaurine and/or salts thereof.

9. The method as claimed in claim 1, wherein an amount of taurine is between 50 and 150 mg/day in the form of taurine and/or hypotaurine and/or salts thereof.

10. The method as claimed in claim 1, wherein the salts of taurine and/or hypotaurine are the magnesium, manganese, iron II or zinc salts.

11. The method as claimed in claim 1, wherein the oral composition further comprises at least one fatty acid.

12. The method as claimed in claim 11, wherein the fatty acid is selected from the group consisting of n-6 and n-3 essential polyunsaturated fatty acids containing between 18 and 22 carbon atoms, esters thereof, and mixtures thereof.

13. The method as claimed in claim 11, wherein the fatty acid is selected from the group consisting of linoleic acid, γ-linolenic acid, linolenic acid, stearidonic acid, crocetin, 5,8,11,14-eicosatetraenoic acid, and mixtures thereof.

14. The method as claimed in claim 11, wherein the daily dose of the fatty acid is between 0.5 and 3500 mg/day.

15. The method as claimed in claim 11, wherein the fatty acid is at least one n-6 fatty acid in an amount of 0.5 to 2600 mg/day.

16. The method as claimed in claim 11, wherein the fatty acid is at least one n-3 fatty acid in an amount of 0.5 to 2500 mg/day.

17. The method as claimed in claim 1, wherein the oral composition is in the form of a food supplement.

18. The method as claimed in claim 1, wherein the daily dose of the polyphenol is between 0.5 and 2000 mg/day.

19. The method as claimed in claim 1, wherein the daily dose of the polyphenol is from about 0.5 to 1000 mg/day.

20. The method as claimed in claim 1, wherein the oral composition further comprises at least one supplement selected from the group consisting of vitamins C and E, zinc and salts thereof, selenium, and carotenoids.

21. The method as claimed in claim 1, wherein the polyphenol/taurine weight ratio is greater than or equal to 0.75.

22. The method as claimed in claim 1, wherein said composition comprises 0.01% to 30% by weight of taurine and/or hypotaurine and/or salts thereof, in combination with 0.1% to 50% by weight of extracts comprising said at least one polyphenol.

23. The method as claimed in claim 1, wherein said composition is free of vitamin C.

24. The method as claimed in claim 1, wherein said at least one polyphenol is mixture of catechin monomers with procyanidin oligomers, in an amount effective for treating miniaturization of the hair follicle.

25. A cosmetic process for treating miniaturization of the hair follicle via the oral administration of an oral composition comprising taurine and/or hypotaurine and/or acceptable salts thereof; and at least one polyphenol, said polyphenol being selected from the group consisting of procyanidins, proanthocyanidins, a mixture of catechin monomers with procyanidin oligomers, and mixtures thereof, a weight ratio of polyphenol/taurine being at least 0.5;
wherein the taurine and/or hypotaurine and/or acceptable salts thereof are the only active amino acid administered.

26. The process as claimed in claim 25, in which the taurine, hypotaurine and/or acceptable salts thereof is (are) administered at a dose of from 0.5 to 4000 mg per day of taurine.

27. The process as claimed in claim 25, in which the taurine, hypotaurine and/or acceptable salts thereof is (are) used in combination with at least one supplement selected from the group consisting of zinc, fatty acids, vitamin C, vitamin E, and carotenoids.

28. The method as claimed in claim 25, wherein said at least one polyphenol is a mixture of catechin monomers with procyanidin oligomers in an amount effective for treating miniaturization of the hair follicle.

29. A cosmetic process for treating disorders of a pilosebaceous unit via oral administration of at least one fatty acid, at least one polyphenol or an extract comprising the same, said polyphenol being selected from the group consisting of procyanidins, proanthocyanidins, a mixture of catechin monomers with procyanidin oligomers, and mixtures thereof, in combination with at least one of taurine, hypotaurine, salts of taurine and salts of hypotaurine, a weight ratio of polyphenol/taurine being at least 0.5, wherein the taurine, hypotaurine, and salts thereof are the sole active amino acid.

30. The process as claimed in claim 29, in which the taurine, hypotaurine or acceptable salts thereof is (are) administered at a dose of from 0.5 to 4000 mg/day, as taurine equivalent, and the at least one fatty acid is administered at a dose of from 0.5 to 5400 mg/day, and the at least one polyphenol is administered at a dose of from 0.5 to 2000 mg/day.

31. A composition for oral absorption, comprising:
a total amount of at least 0.05% to 80% by weight of at least one of taurine, hypotaurine, salts of taurine and salts of hypotaurine as an active agent, the salts being acceptable for oral absorption, at least one polyphenol, said polyphenol being selected from the group consisting of procyanidins, proanthocyanidins, a mixture of catechin monomers with procyanidin oligomers, and mixtures thereof, a weight ratio of polyphenol/taurine being at least 0.5, and an excipient, said composition being free of vitamin C, wherein the taurine, hypotaurine, and salts thereof are the sole active amino acid.

32. The composition as claimed in claim 31, further comprising at least one fatty acid and/or a salt thereof acceptable in an oral composition.

33. The composition as claimed in claim 32, wherein said composition comprises from 0.01% to 10% by weight of said at least one polyphenol and/or 0.1% to 10% by weight of said at least one fatty acid.

34. The composition as claimed in claim 33, further comprising at least one compound selected from the group consisting of vitamin E, zinc, zinc salts, selenium and carotenoids.

35. The composition as claimed in claim 34, wherein the compound comprises at least one carotenoid selected from the group consisting of β-carotene, lycopene, zeaxanthin, and lutein.

36. The composition as claimed in claim 33, wherein said composition comprises an excipient that is acceptable for a food supplement in the form of a sugarcoated tablet, a gel capsule, a gel, an emulsion, a tablet, a wafer capsule, a drinkable ampule, a dilutable or nondilutable powder, a dietary bar or an enriched food.

37. The composition as claimed in claim 32, wherein said composition comprises 0.01% to 30% by weight of taurine and/or hypotaurine and/or acceptable salts thereof, in combination with 0.1% to 50% by weight of extracts comprising said at least one polyphenol.

38. The composition as claimed in claim 31, wherein said composition is a food supplement.

39. The composition as claimed in claim 31, wherein the polyphenol/taurine weight ratio is greater than or equal to 0.75.

40. The composition as claimed in claim 31, wherein the polyphenol/taurine weight ratio is greater than or equal to 1.

41. A composition for oral absorption, comprising:
at least one polyphenol selected from the group consisting of procyanidins, proanthocyanidins, a mixture of catechin monomers with procyanidin oligomers, and mixtures thereof;
a fatty acid selected from the group consisting of n-6 and n-3 essential polyunsaturated fatty acids containing between 18 and 22 carbon atoms, esters thereof, and mixtures thereof; and
at least one of taurine, hypotaurine, salts of taurine and salts of hypotaurine, the salts being acceptable for oral absorption, a weight ratio of polyphenol/taurine being at least 0.5;
wherein the taurine, hypotaurine, and salts thereof are the sole active amino acid.

42. The composition as claimed in claim 41, wherein said composition comprises catechins.

43. The composition as claimed in claim 42, wherein said composition comprises 0.01% to 30% by weight of said taurine and/or hypotaurine and/or acceptable salts thereof; in combination with 0.1% to 25% by weight of said catechins.

44. A composition for oral absorption, comprising 0.01% to 30% by weight of at least one of taurine, hypotaurine, salts of taurine and salts of hypotaurine, 0.01% to 10% by weight of fatty acids, and at least one polyphenol, said polyphenol being selected from the group consisting of procyanidins, proanthocyanidins, a mixture of catechin monomers with procyanidin oligomers, and mixtures thereof, a weight ratio of polyphenol/taurine being at least 0.5, wherein the at least one of taurine, hypotaurine, and salts thereof are the sole active amino acid.

* * * * *